(12) United States Patent
Kim et al.

(10) Patent No.: US 11,123,314 B2
(45) Date of Patent: Sep. 21, 2021

(54) PHARMACEUTICAL COMPOSITION FOR PREVENTING AND TREATING PANCREATIC CANCER, CONTAINING GOSSYPOL AND PHENFORMIN AS ACTIVE INGREDIENTS

(71) Applicant: NATIONAL CANCER CENTER, Gyeonggi-do (KR)

(72) Inventors: Soo Youl Kim, Gyeonggi-do (KR); Sang Myung Woo, Seoul (KR); Woo Jin Lee, Seoul (KR); Tae Hyun Kim, Seoul (KR); Sang Jae Park, Gyeonggi-do (KR); Ju Hee Lee, Seoul (KR); Sung Sik Han, Seoul (KR); Eun Kyung Hong, Gyeonggi-do (KR)

(73) Assignee: NATIONAL CANCER CENTER, Gyeonggi-do (KR)

( * ) Notice: Subject to any disclaimer, the term of this patent is extended or adjusted under 35 U.S.C. 154(b) by 0 days.

(21) Appl. No.: 16/487,831

(22) PCT Filed: Feb. 22, 2018

(86) PCT No.: PCT/KR2018/002172
§ 371 (c)(1),
(2) Date: Aug. 21, 2019

(87) PCT Pub. No.: WO2018/155921
PCT Pub. Date: Aug. 30, 2018

(65) Prior Publication Data
US 2020/0246283 A1 Aug. 6, 2020

(30) Foreign Application Priority Data
Feb. 22, 2017 (KR) .................. 10-2017-0023406

(51) Int. Cl.
| | | |
|---|---|---|
| A61K 31/155 | (2006.01) | |
| A61K 31/4745 | (2006.01) | |
| A61K 31/7068 | (2006.01) | |
| A61K 31/337 | (2006.01) | |
| A61P 35/00 | (2006.01) | |
| A61K 9/00 | (2006.01) | |
| A61K 31/12 | (2006.01) | |

(52) U.S. Cl.
CPC .......... *A61K 31/155* (2013.01); *A61K 9/0053* (2013.01); *A61K 31/12* (2013.01); *A61K 31/337* (2013.01); *A61K 31/4745* (2013.01); *A61K 31/7068* (2013.01); *A61P 35/00* (2018.01)

(58) Field of Classification Search
CPC ...... A61K 9/0059; A61K 31/11; A61K 31/12; A61K 31/155; A61K 31/337; A61K 31/4745; A61K 31/7068; A61P 35/00
USPC .......................................... 514/49
See application file for complete search history.

(56) References Cited

U.S. PATENT DOCUMENTS

| | | | |
|---|---|---|---|
| 2009/0082445 A1 | 3/2009 | Wang et al. | |
| 2009/0175869 A1* | 7/2009 | Holmlund ............ | A61K 31/437 424/138.1 |
| 2012/0114676 A1* | 5/2012 | Thompson .............. | A61P 35/02 424/184.1 |
| 2017/0071877 A1 | 3/2017 | Kim et al. | |
| 2019/0254995 A1 | 8/2019 | Kang et al. | |

FOREIGN PATENT DOCUMENTS

IN 201627031244 A 10/2016

OTHER PUBLICATIONS

The Merck Manual, 1992, 16th Ed., pp. 1263 and 1266-1269.*
Bailey et al., Targeting the metabolic microenvironment of tumors, Adv. Pharmacol., 65:63-107 (2012).

* cited by examiner

*Primary Examiner* — Ganapathy Krishnan
(74) *Attorney, Agent, or Firm* — Marshall, Gerstein & Borun LLP

(57) ABSTRACT

The present disclosure relates to a pharmaceutical composition comprising a combination of anticancer agents, capable of creating a synergistic effect when co-administer in the treatment of cancer, and more specifically, the present invention suggests anticancer agents capable of creating a synergistic effect when co-administered with gossypol and phenformin. The anticancer agents selected as said anticancer agents in the present disclosure are sorafenib, vemurafenib, irinotecan, cisplatin, paclitaxel, and doxorubicin, and each of the aforementioned anticancer agent, when co-administered as a triple-drug combination with gossypol and phenformin can provide a significant synergistic effect in terms of the effect of suppressing the proliferation of cancer and killing cancer cell, compared to each mono-drug treatment group and a dual-drug treatment group of gossypol+phenformin.

4 Claims, 16 Drawing Sheets

[FIG. 1]
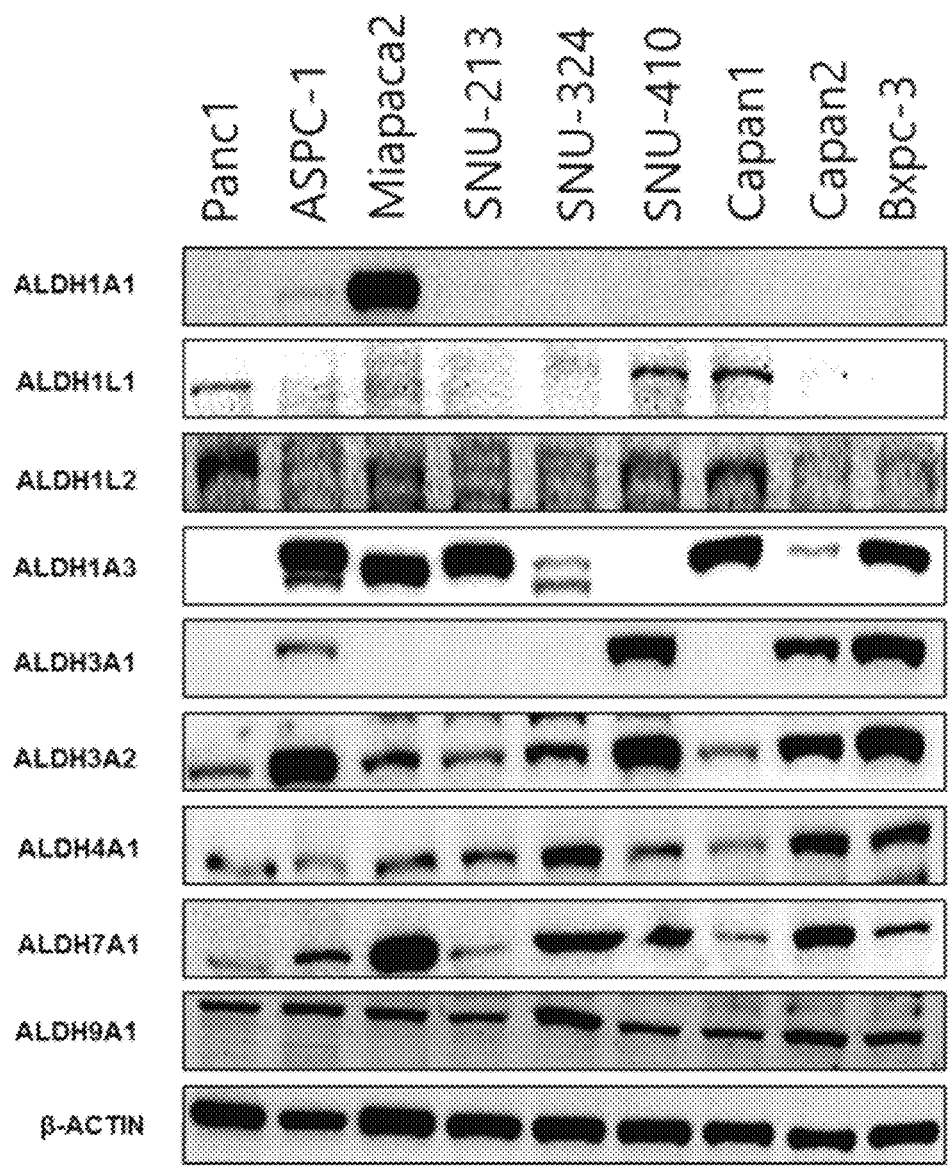

[FIG. 2]
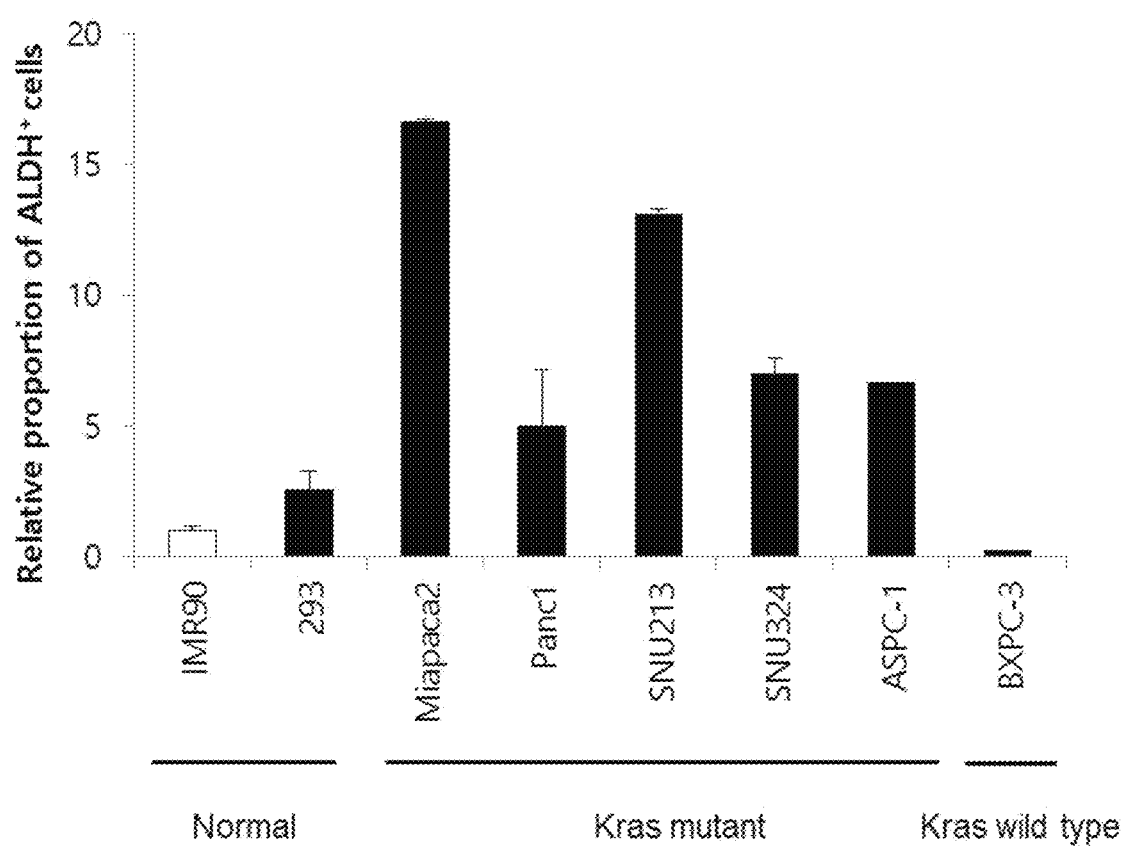

[FIG. 3]
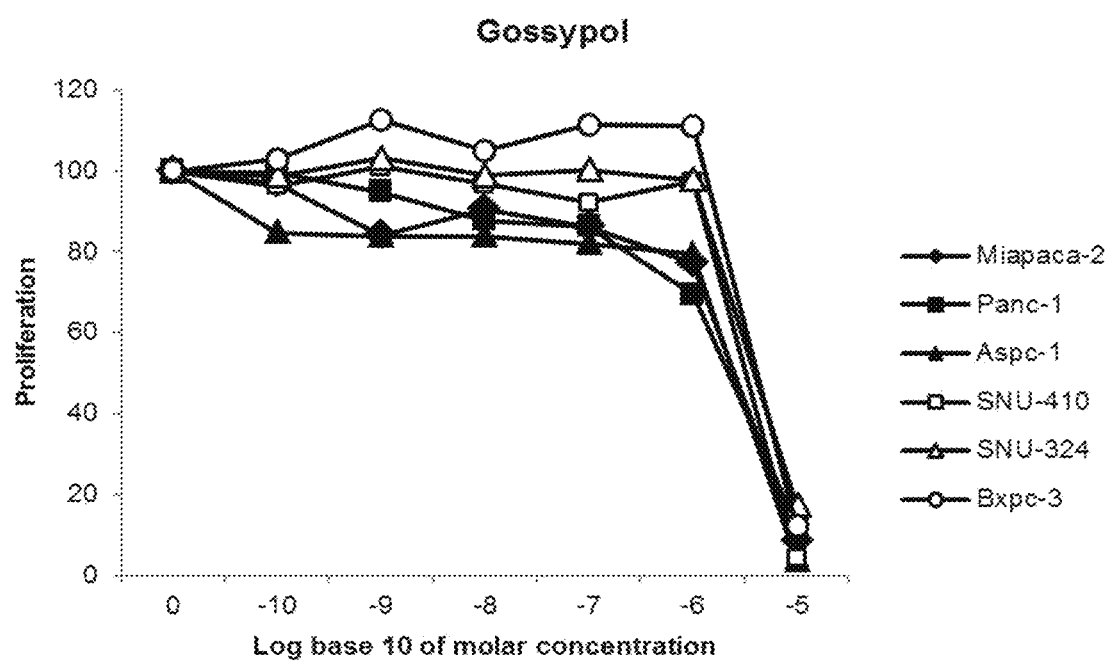
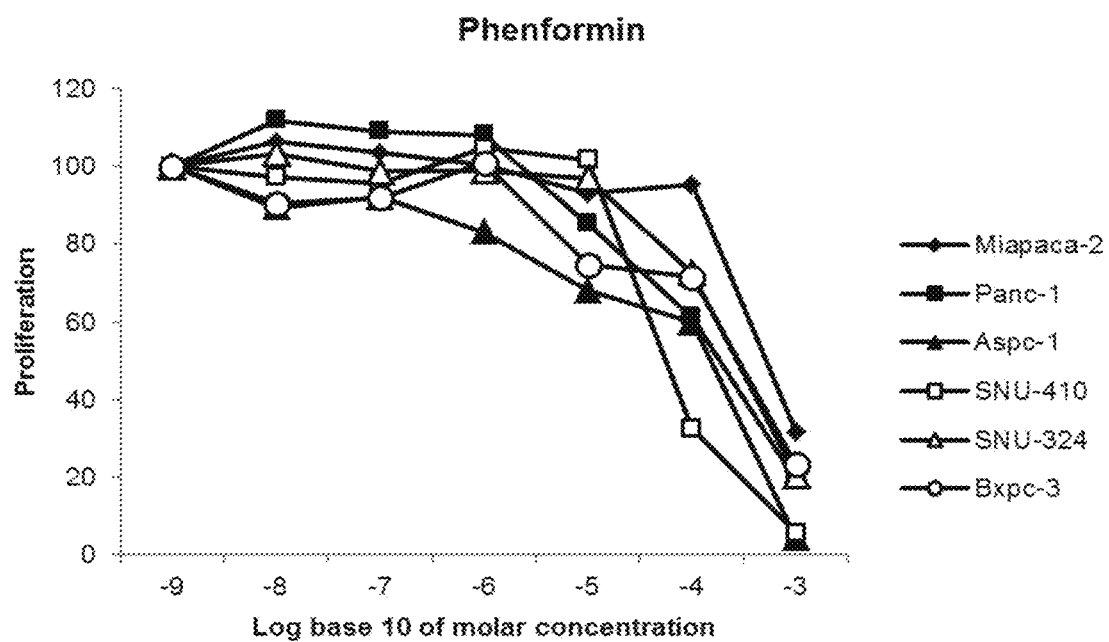

[FIG. 4A]
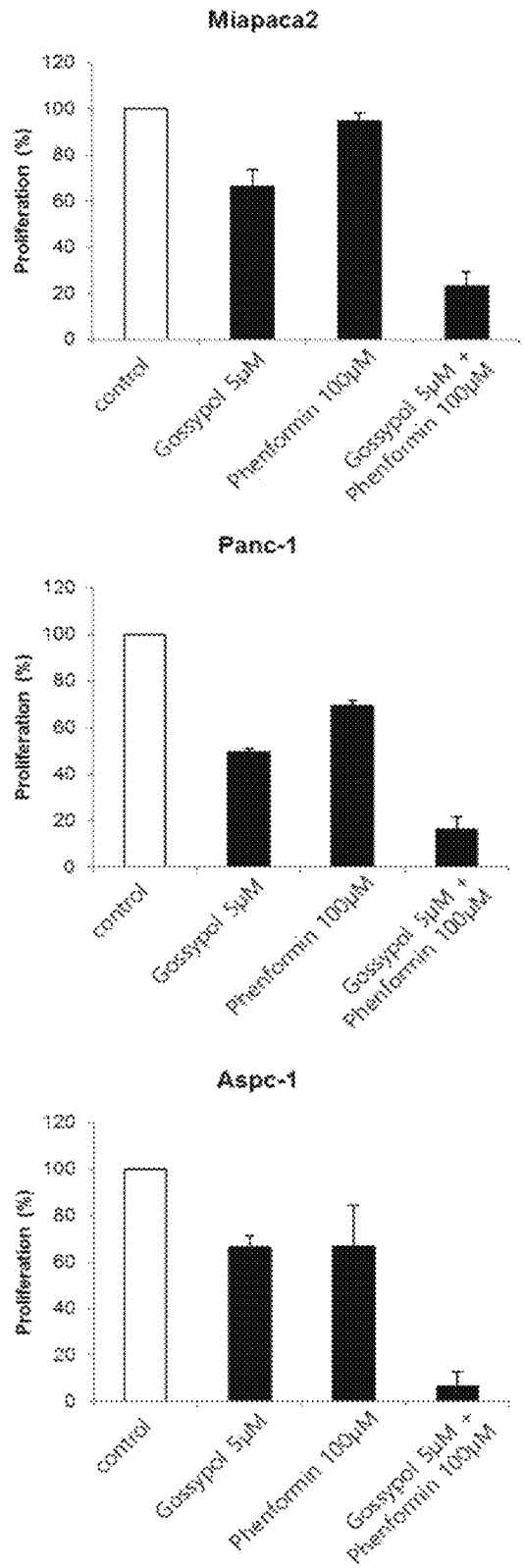

[FIG. 4B]
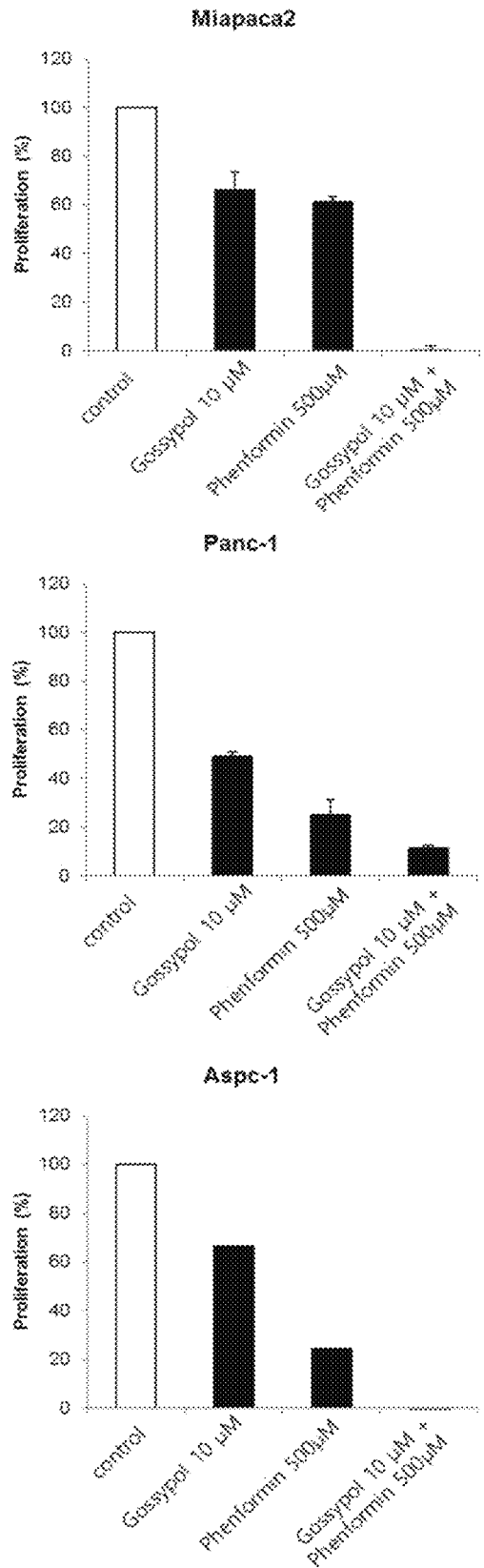

[FIG. 5A]
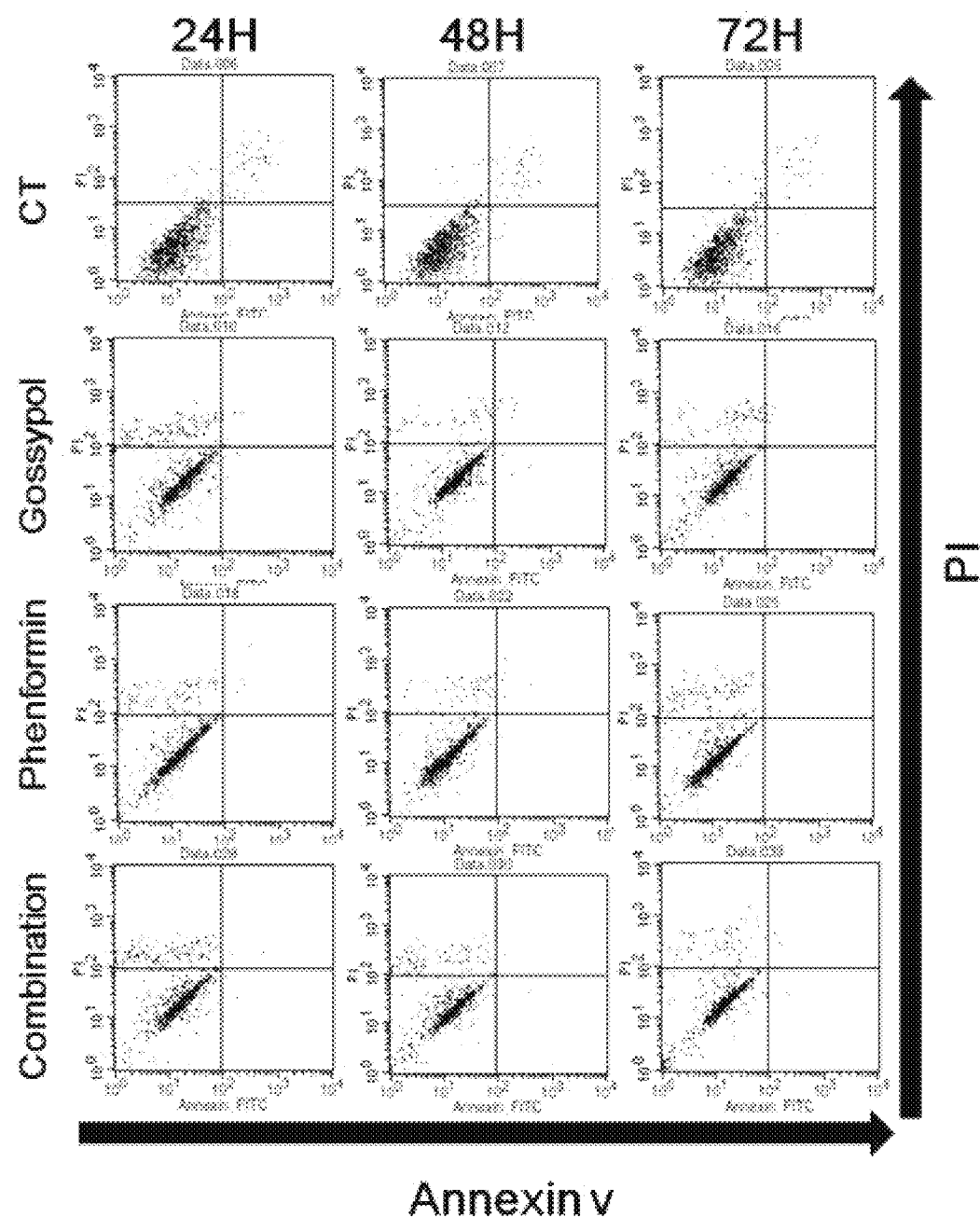

【FIG. 5B】
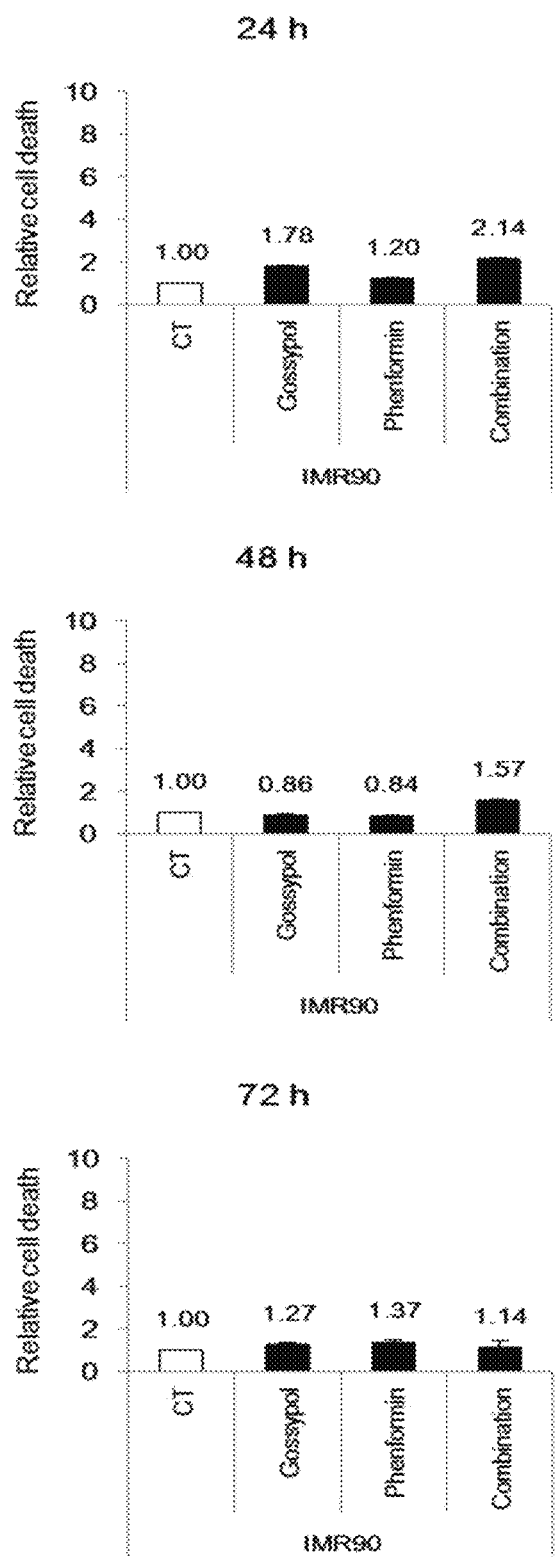

[FIG. 6]
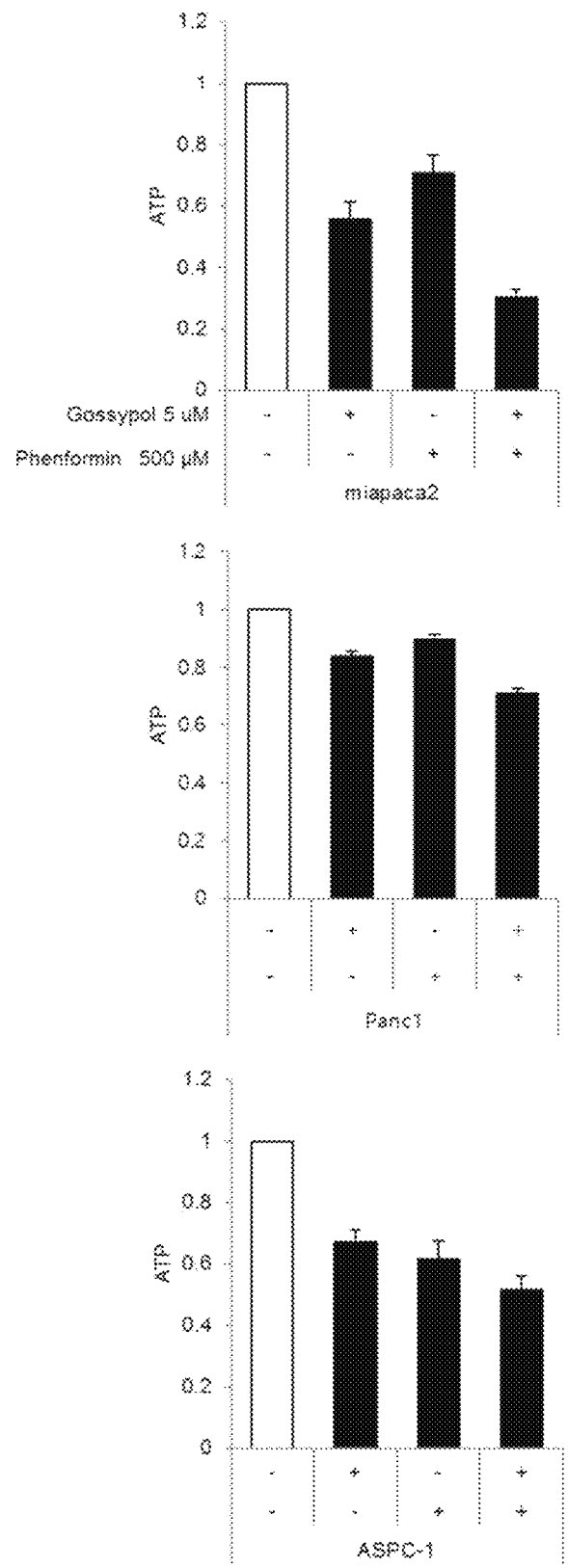

[FIG. 7A]
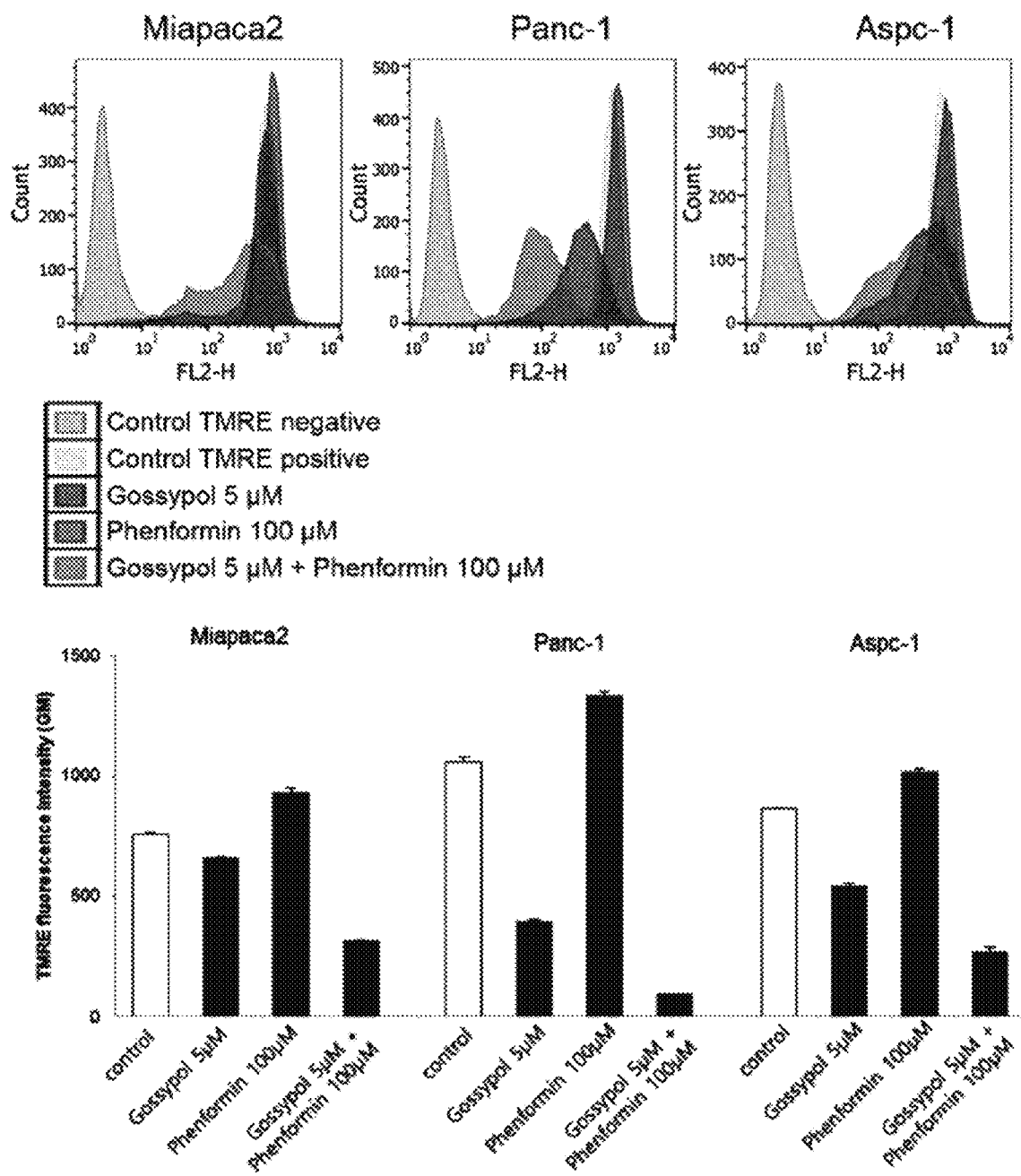

[FIG. 7B]
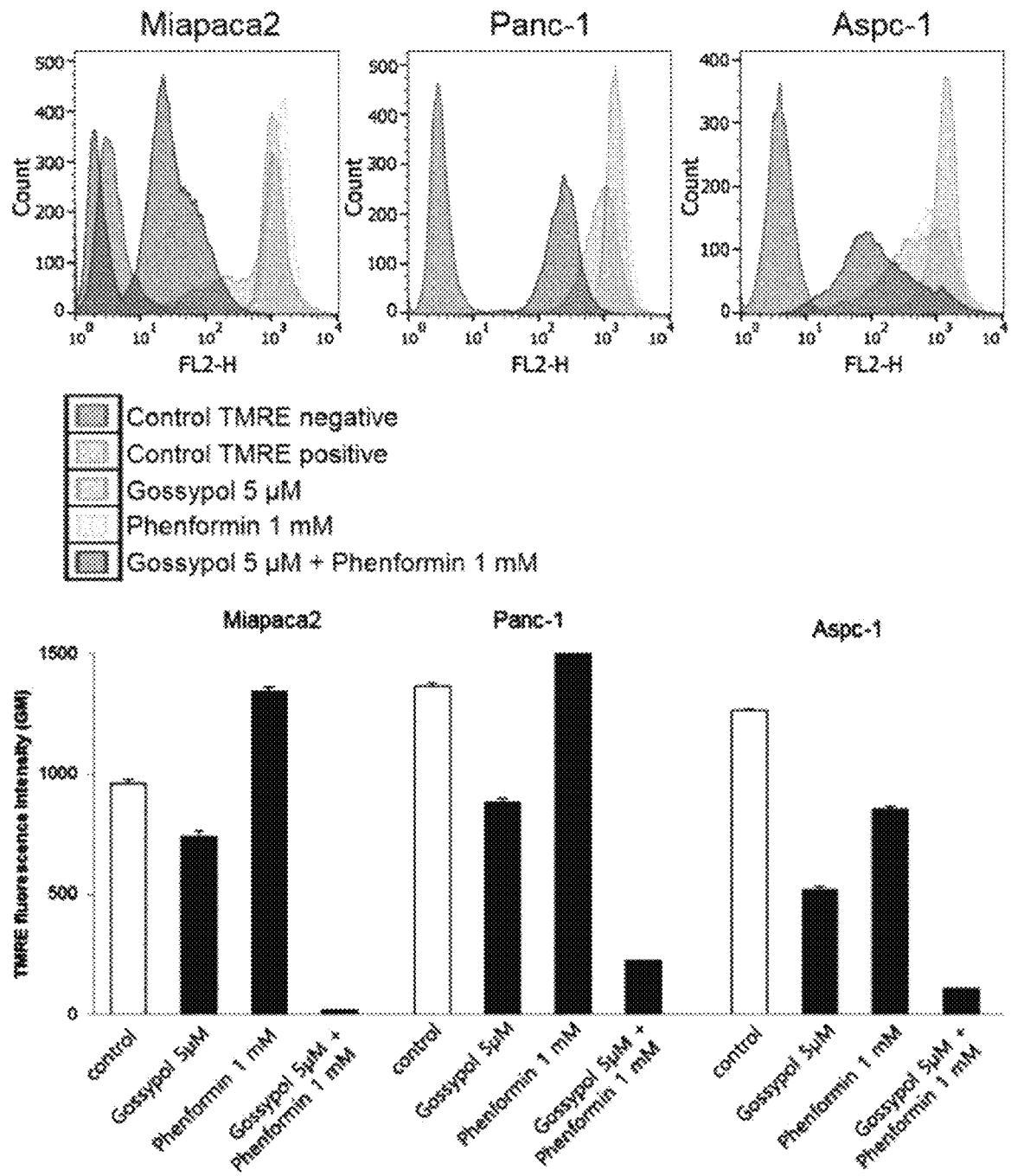

[FIG. 8]
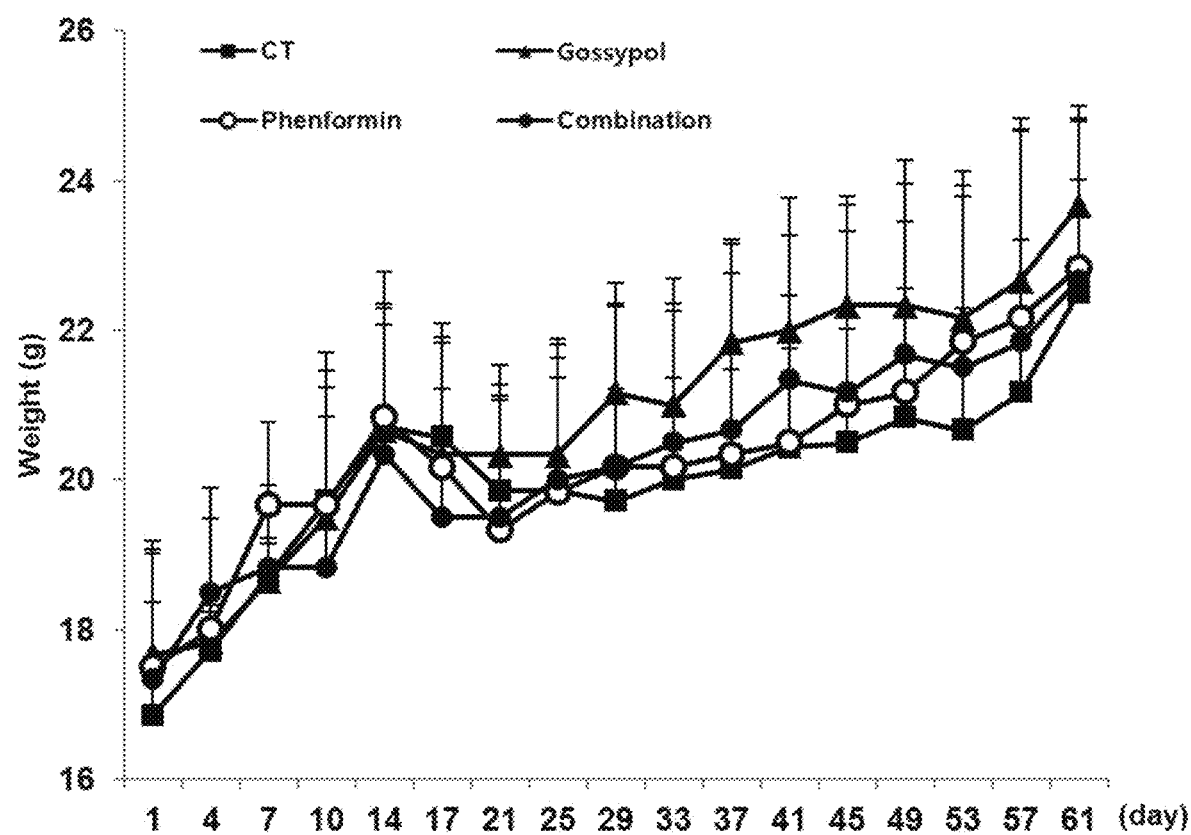

[FIG. 9A]
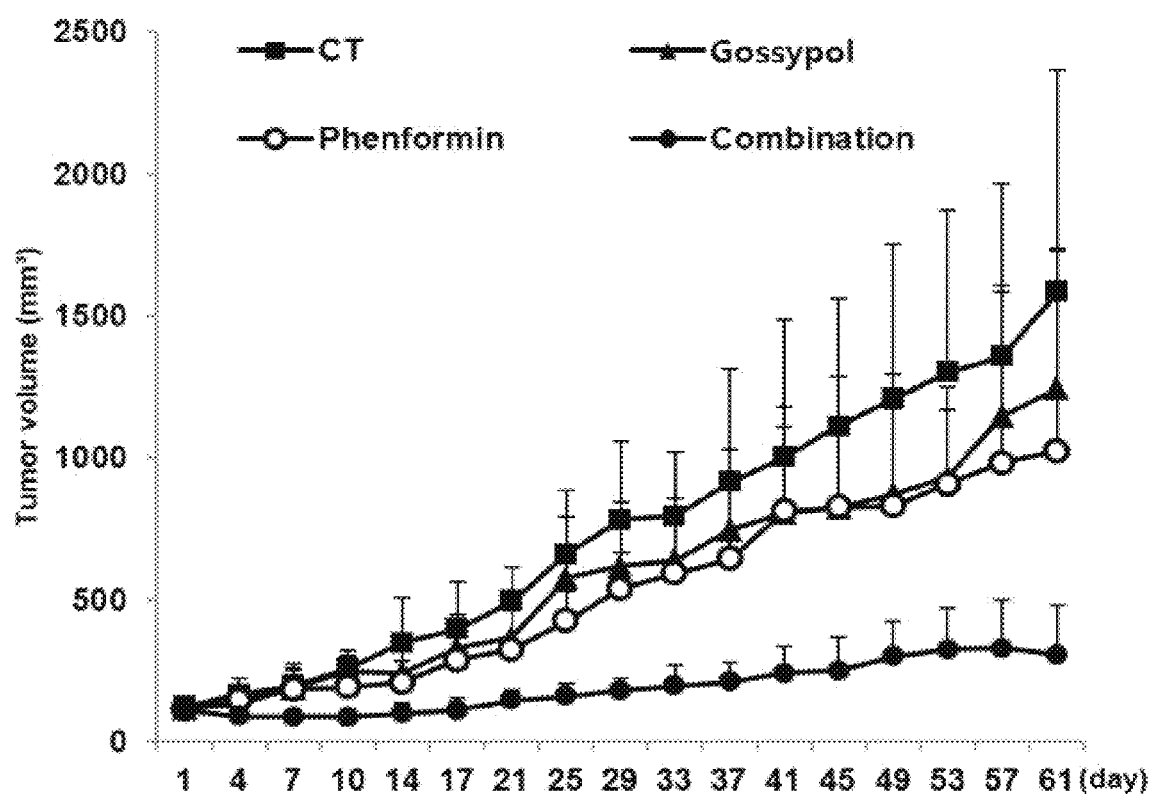

[FIG. 9B]
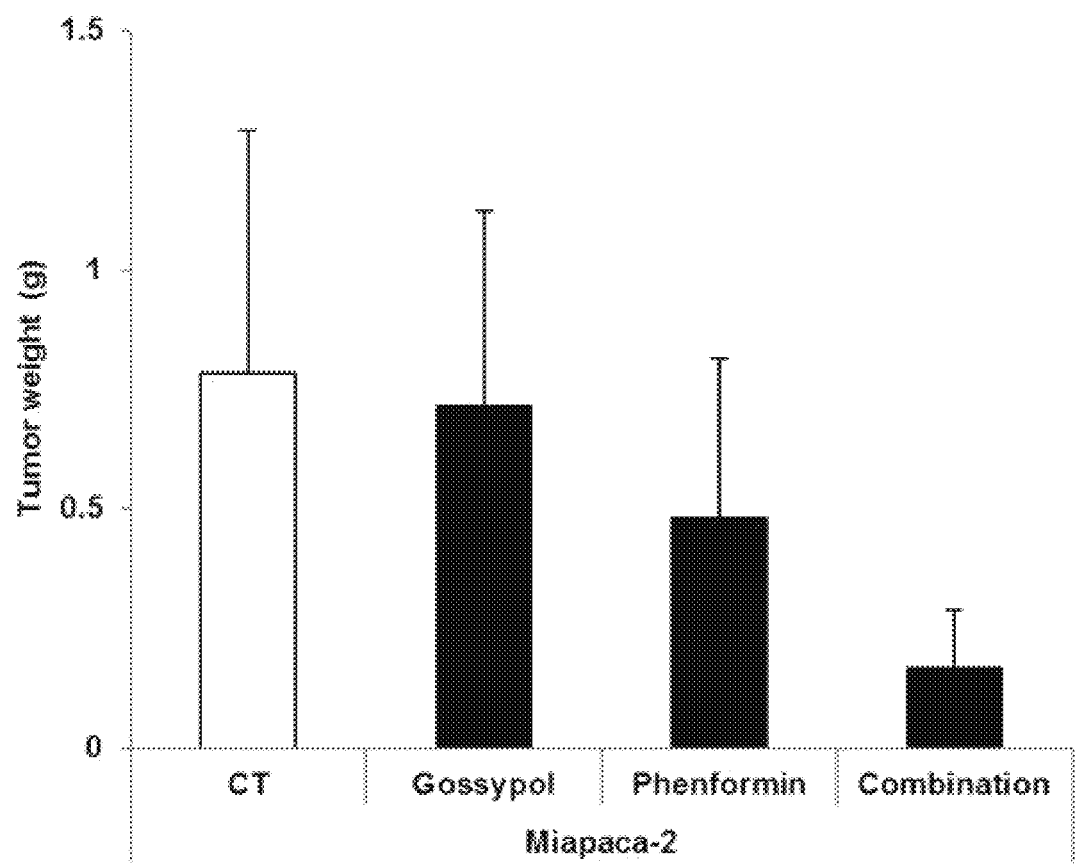

[FIG. 9C]
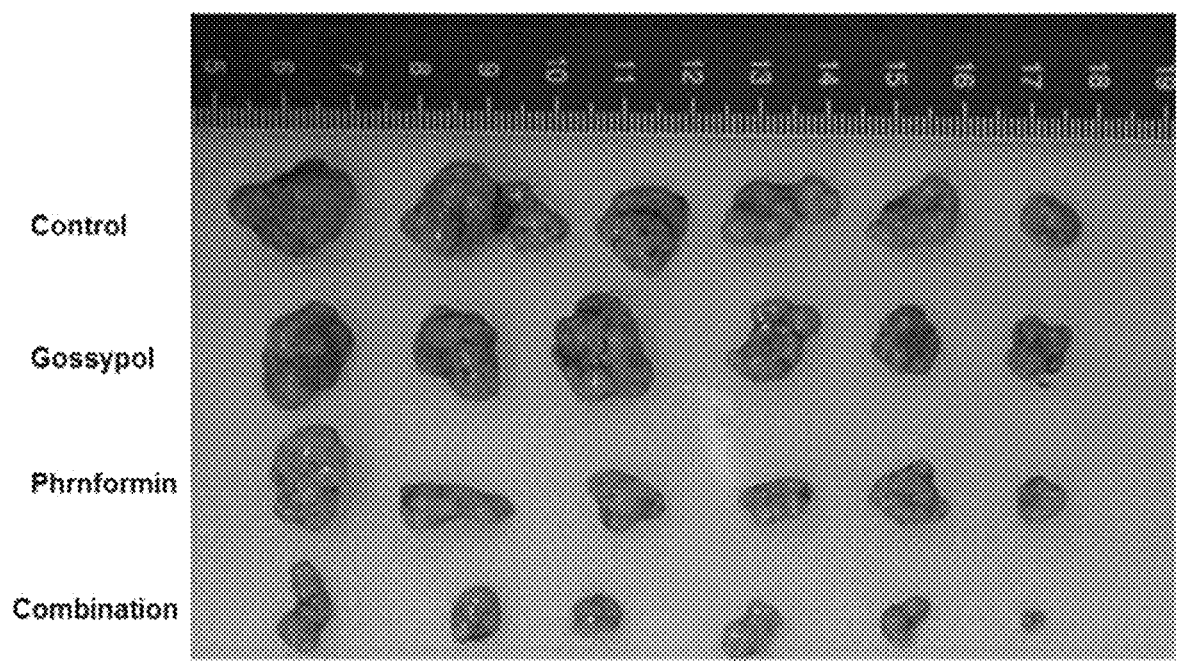

[FIG. 10A]
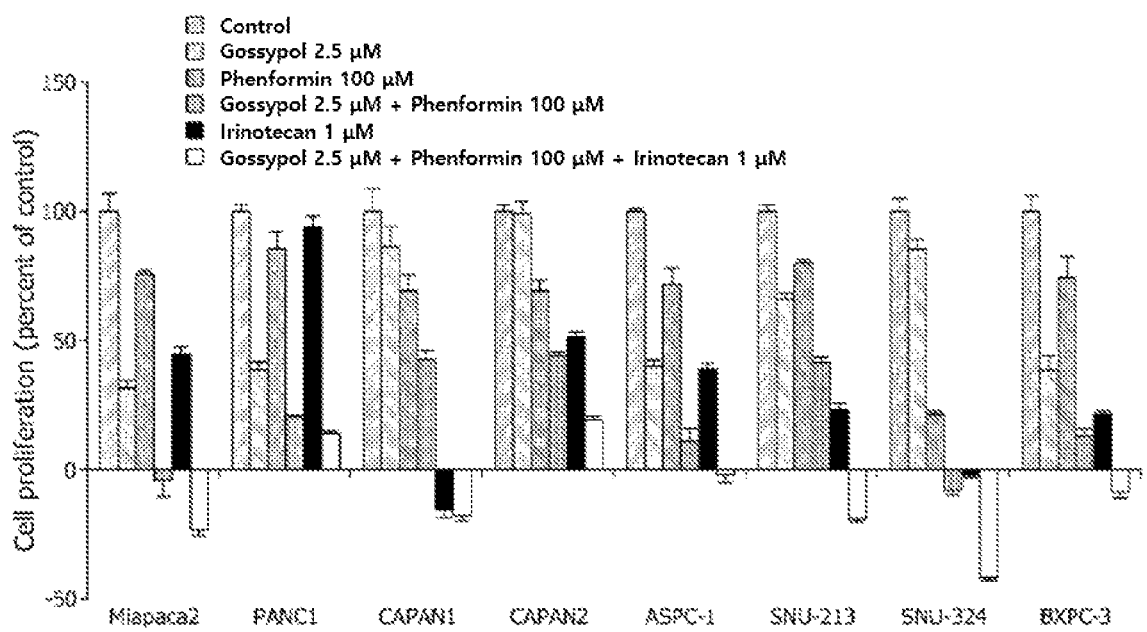
[FIG. 10B]
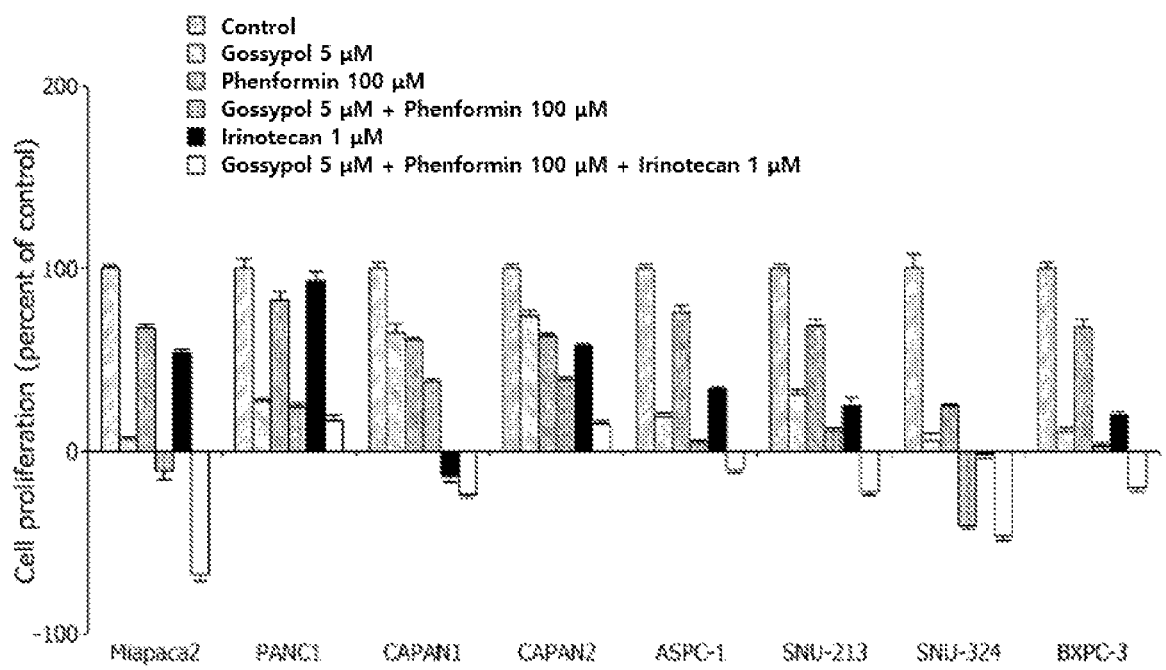

[FIG. 11A]
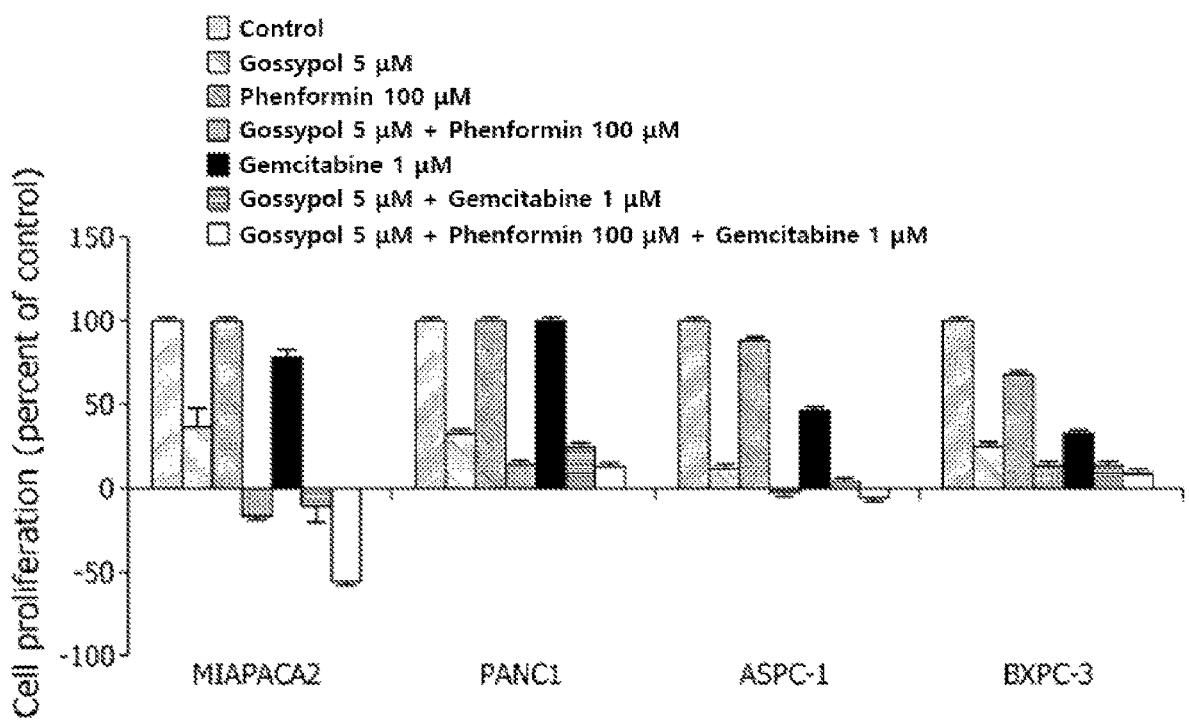
[FIG. 11B]
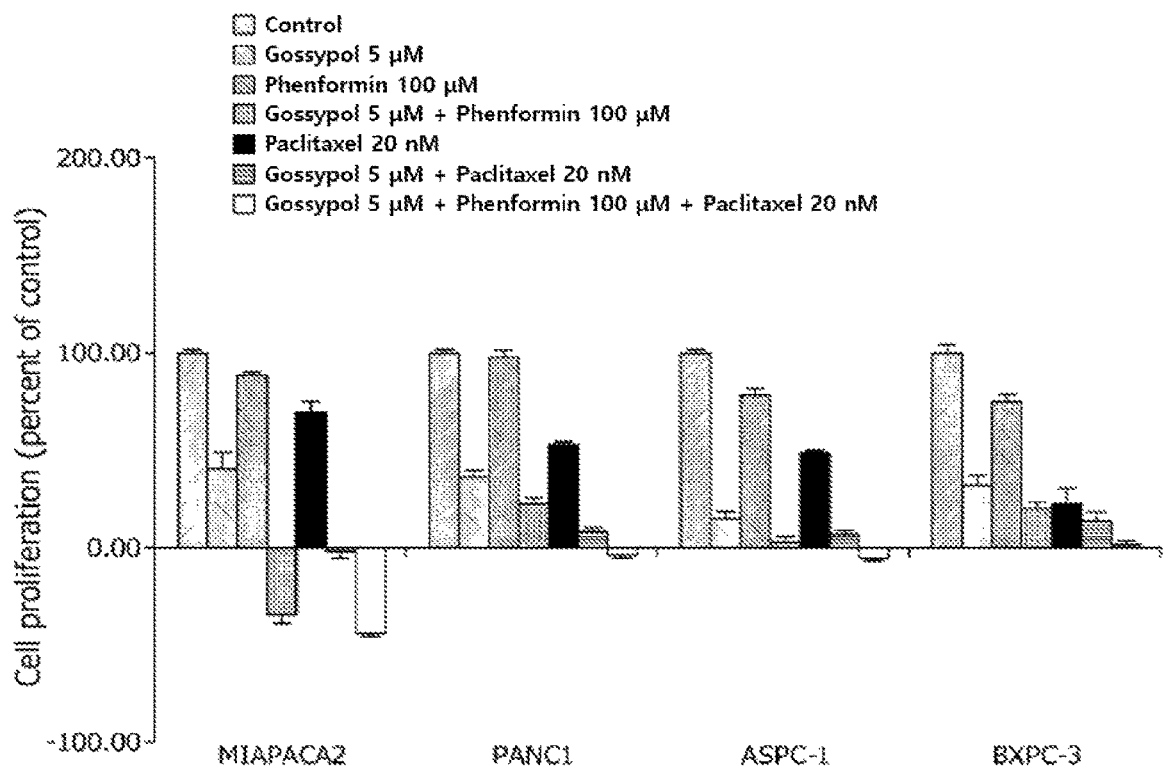

PHARMACEUTICAL COMPOSITION FOR PREVENTING AND TREATING PANCREATIC CANCER, CONTAINING GOSSYPOL AND PHENFORMIN AS ACTIVE INGREDIENTS

TECHNICAL FIELD

The present application claims priority to Korean Patent Application No. 10-2017-0023406 filed on Feb. 22, 2017, the entirety of which is incorporated herein by reference.

The present invention provides a pharmaceutical composition containing gossypol and phenformin, capable of exhibiting a synergistic effect in the treatment of pancreatic cancer.

BACKGROUND ART

Cancer, also called tumor, is a mass of cells composed of undifferentiated cells which proliferate in an unlimited manner irrespective of conditions required in tissues, unlike normal cells which can proliferate in a regular and controllable manner and can be suppressed, according to the individual's needs. Cancer cells, which proliferate in such an unlimited manner, penetrate into surrounding tissues and, in a worse case, metastasize to other organs of the body, thereby causing an intractable disease that involves severe pain and eventually leads to death.

Cancer is largely classified into blood cancer and solid cancer, and develops in almost all parts of the body as in pancreatic cancer, breast cancer, oral cancer, liver cancer, uterine cancer, esophageal cancer, skin cancer, and the like. As therapeutic methods therefor, a small number of targeted therapeutic agents such as Gleevec or Herceptin have recently been used to treat certain cancers. However, up to now, surgery or radiation therapy and anti-cancer agent therapy using a chemotherapeutic agent that inhibits cell proliferation are mainly used methods. However, conventional chemotherapeutic agents are not targeted therapeutic agents. Thus, the biggest problem of the conventional chemotherapeutic agents is a side effect due to their cytotoxicity and drug resistance, which are the main factors that eventually result in failure of treatment despite initial successful response caused by anti-cancer agents. Therefore, in order to overcome limitations of these chemotherapeutic agents, there is a need to continuously develop a targeted therapeutic agent having a clear mechanism of anti-cancer action.

Among these, pancreatic cancer is ranked as the $7^{th}$ leading cause of cancer deaths worldwide, and is reported as the $5^{th}$ leading cause of death in Korea. Pancreatic cancer is an aggressive disease as compared with cancer diseases of other parts such as uterine cancer, breast cancer, rectal cancer, colorectal cancer, skin cancer, lung cancer, and liver cancer. However, pancreatic cancer has a disadvantage of being very difficult to make a diagnosis. In addition, pancreatic cancer is one of the most serious malignant tumors with acute onset, delayed diagnosis, and low survival rate. Therefore, other types of cancers such as lung cancer have an increased average survival rate, whereas pancreatic cancer rather tends to have a decreased survival rate due to difficulty of diagnosis and treatment.

In a case of being compared with lung cancer which is the most common type of cancer, pancreatic cancer not only has a fundamental difference that the organ in which cancer develops is different, but also has a difference in terms of treatment due to different clinical pathological features and molecular biological features thereof. From a molecular biological point of view, it is reported that mutation of ras gene, which is an oncogene, is seen in most (about 90%) of pancreatic cancers, which may lead to different therapeutic perspectives for pancreatic cancer, as compared to lung cancer or the like, for which mutation of the ras oncogene is seen in a low proportion of 10%. In addition, most pancreatic cancer patients exhibit very aggressive course of progression and biological features as compared with lung cancer patients, thereby being at risk of leading to a poor prognosis. Pancreatic cancer patients are locally advanced, have many difficulties to perform resection, usually show a metastatic disease, and often respond sensitively to side effects caused by intensive therapy. Only 10% to 15% of patients are treatable with surgical resection. Even after fundamental treatment with surgery, a rate of recurrence remains very high.

Therefore, development of anti-cancer agents that can treat pancreatic cancer in a more effective manner, and research on therapeutic strategies using the same have been continuously carried out. However, in a range actually applied in clinical practice, targeted therapeutic agents or immunotherapeutic agents, which have recently attracted attention, have limitations of being applied to representative cancer diseases such as lung cancer, breast cancer, and gastric cancer. On the contrary, many cases where the same effect is not exhibited in pancreatic cancer have been reported. Accordingly, there is a growing demand for new therapeutic strategies against pancreatic cancer.

Gossypol is a naturally-occurring double biphenolic compound derived from crude cottonseed oil (*Gossypium* sp.). Gossypol is known to be an inhibitor for aldehyde dehydrogenase (ALDH) in vivo and has been studied for its therapeutic use. Human clinical trials for gossypol as a male contraceptive have been reported to demonstrate safety of long-term administration of this compound.

Phenformin is a biguanide-based drug such as metformin, and is known to be a therapeutic agent for diabetes. However, as it has become known that biguanide-based drugs such as phenformin activate AMP-activated protein kinase (AMPK), a key enzyme for physiologically regulating carbohydrate metabolism and lipid metabolism, and thus are effective in the treatment of cancer that lacks p53 gene, studies on anti-cancer effects of phenformin drugs have been conducted and potential for phenformin to have an anti-cancer effect has been proven.

As described above, while the anti-cancer effect of each of gossypol and phenformin is known, a synergistic effect exhibited in a case where these compounds are applied in combination to pancreatic cancer has not been studied yet.

Therefore, as a result of efforts to find a therapeutic agent for pancreatic cancer which can exhibit a synergistic anti-cancer effect even at a small dose, the present inventors have identified that a significantly increased synergistic effect can be exhibited, in terms of inhibitory effects on growth of pancreatic cancer cells, in a case where gossypol and phenformin are mixed and applied in combination, as compared with a case where each compound is applied alone; and the present inventors have identified that even in a pancreatic cancer mouse model, a synergistic effect can be exhibited, in terms of increase of tumor weight and volume, in a case of combined administration of gossypol and phenformin. In addition, the present inventors have identified that an inhibitory effect on proliferation of pancreatic cancer can be further remarkably increased in a case where gossypol and phenformin are mixed with irinotecan, gemcitabine, or paclitaxel, and the resulting triple combination drug is applied to pancreatic cancer, thereby identifying that a pharmaceutical composition containing gossypol and phenformin of the present invention can exhibit a synergistic anti-pancreatic cancer effect in the treatment of pancreatic cancer even in case where each of the drugs is administered in a small amount; and thus have completed the present invention.

DISCLOSURE

Technical Problem

Therefore, the present inventors have identified that a significant synergistic effect can be exhibited, in terms of therapeutic effects on pancreatic cancer, in a case where gossypol and phenformin are administered in combination, as compared with a case where each of these compounds is administered alone, and thus have completed the present invention.

Accordingly, an object of the present invention is to provide a pharmaceutical composition for preventing and treating pancreatic cancer.

Technical Solution

In order to achieve the above object, the present invention provides a pharmaceutical composition for preventing and treating pancreatic cancer, containing gossypol and phenformin as active ingredients.

In addition, the present invention provides a pharmaceutical composition for preventing and treating pancreatic cancer, containing gossypol and phenformin, with an anti-cancer agent further contained.

In addition, the present invention provides a method for preventing or treating pancreatic cancer, comprising a step of administering effective amounts of gossypol and phenformin to an individual in need thereof.

In addition, the present invention provides a method for preventing or treating pancreatic cancer, comprising a step of administering effective amounts of gossypol and phenformin, with an anti-cancer agent further contained, to an individual in need thereof.

In addition, the present invention provides a use of a pharmaceutical composition containing gossypol and phenformin as active ingredients, for use in the prevention and treatment of pancreatic cancer.

In addition, the present invention provides a use of a pharmaceutical composition containing gossypol and phenformin, with an anti-cancer agent further contained, for use in the prevention and treatment of pancreatic cancer.

In a preferred embodiment of the present invention, the gossypol may be a compound represented by the following Formula 1, and the phenformin may be a compound represented by the following Formula 2:

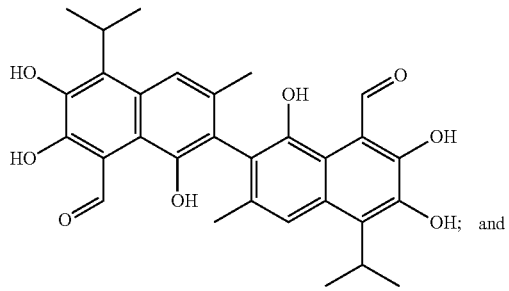

[Formula 1]

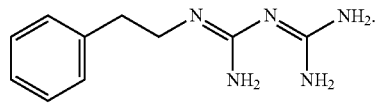

[Formula 2]

In a preferred embodiment of the present invention, the gossypol and the phenformin may be mixed in a molar ratio of 1:10 to 1:500.

In a preferred embodiment of the present invention, the further contained anti-cancer agent may be at least one selected from the group consisting of irinotecan, gemcitabine, and paclitaxel.

Advantageous Effects

Accordingly, the present invention provides a pharmaceutical composition for preventing and treating pancreatic cancer, containing gossypol and phenformin as active ingredients.

In the present invention, gossypol is an inhibitor of ALDH expression and activity and serves to induce intracellular ATP deficiency so that cancer cells can be killed; and phenformin is an inhibitor for the mitochondrial complex I and decreases the mitochondrial membrane potential so that a synergistic effect can be exhibited in an ATP deficiency phenomenon. Thus, it is possible to provide a significantly increased inhibitory effect on growth of pancreatic cancer in a case where gossypol and phenformin are applied in combination, as compared with a case where each of these compounds is applied alone.

In addition, it is possible to provide a significantly increased inhibitory effect on growth of pancreatic cancer in a case where gossypol and phenformin are mixed with irinotecan, gemcitabine, or paclitaxel, and the resulting triple drug is applied, as compared with a case where gossypol and phenformin are applied in combination.

Therefore, in a case of treating pancreatic cancer using the pharmaceutical composition for preventing and treating pancreatic cancer of the present invention, it is possible to achieve a significant inhibitory effect on proliferation of pancreatic cancer cells and tumor growth with only low concentrations of drugs. Thus, the pharmaceutical composition is effective in that it can specifically kill only pancreatic cancer without affecting survival of normal cells.

DESCRIPTION OF DRAWINGS

FIG. 1 illustrates a result obtained by identifying expression levels of isoform proteins of aldehyde dehydrogenase (ALDH) in various pancreatic cancer cell lines.

FIG. 2 illustrates a result obtained by identifying activity of ALDH in various pancreatic cancer cell lines.

FIG. 3 illustrates inhibitory effects on cell proliferation, caused by administration of gossypol or phenformin alone, in various pancreatic cancer cell lines.

FIG. 4 illustrates synergistic inhibitory effects on cell proliferation, caused by combined treatment with gossypol and phenformin, in pancreatic cancer cell lines of Maiapaca2, Panc-1, and Aspc-1:

FIG. 4A illustrates results obtained by identifying inhibitory effects on proliferation of pancreatic cancer cell line in a case where gossypol 5 μM or phenformin 100 μM is applied alone, or gossypol 5 μM and phenformin 100 μM are applied in combination; and FIG. 4B illustrates results obtained by identifying inhibitory effects on proliferation of pancreatic cancer cell line in a case where gossypol 10 μM or phenformin 500 μM is applied alone, or gossypol 10 μM and phenformin 500 μM are applied in combination.

FIG. 5 illustrates results obtained by identifying cell death caused by treatment with gossypol, phenformin, or a mixture thereof in IMR90, a normal cell line:

FIG. 5A illustrates results obtained by identifying, through FITC Annexin V apoptosis detection analysis, cell death over time caused by treatment with gossypol 10 μM or phenformin 100 μM alone, or by combined treatment with gossypol 10 μM and phenformin 100 μM; and FIG. 5B illustrates quantification of the FITC V apoptosis detection analysis results.

FIG. 6 illustrates results obtained by identifying ATP deficiency effects caused by combined treatment with gossypol and phenformin in pancreatic cancer cell lines.

FIG. 7 illustrates mitochondrial membrane potential-decreasing effects caused by combined treatment with gossypol and phenformin in pancreatic cancer cell lines:

FIG. 7A illustrates results obtained by identifying mitochondrial membrane potential-decreasing effects caused in a case where gossypol 5 μM or phenformin 100 μM is applied alone, or in a case where gossypol 5 μM and phenformin 100 μM are applied in combination; and FIG. 7B illustrates results obtained by identifying mitochondrial membrane potential-decreasing effects caused in a case where gossypol 5 μM or phenformin 1 mM is applied alone, or in a case where gossypol 5 μM and phenformin 1 mM are applied in combination.

FIG. 8 illustrates changes in body weight in a group in which gossypol is applied alone, a group in which phenformin is applied alone, and a group (combination) in which gossypol and phenformin are applied in combination, each group using a pancreatic cancer mouse model.

FIG. 9 illustrates tumor growth-decreasing effects in a group in which gossypol is applied alone, a group in which phenformin is applied alone, and a group (combination) in which gossypol and phenformin are applied in combination, each group using a pancreatic cancer mouse model:

FIG. 9A illustrates a result obtained by identifying changes in pancreatic cancer tumor size depending on days of breeding;

FIG. 9B illustrates a result obtained by identifying tumor weights in the respective drug-treated groups after the end of breeding; and FIG. 9C illustrates a result obtained by comparing tumor sizes in the respective drug-treated groups after the end of breeding.

FIG. 10 illustrates synergistic inhibitory effects on proliferation of pancreatic cancer cells, caused by combined treatment with gossypol, phenformin, and irinotecan, in various pancreatic cancer cell lines:

FIG. 10A illustrates a result obtained by identifying inhibitory effects on proliferation of pancreatic cancer cell lines, caused in a case where gossypol 2.5 μM, phenformin 100 μM, or irinotecan 1 μM is applied alone, in a case where gossypol 2.5 μM and phenformin 100 μM are applied in combination, or in a case where gossypol 2.5 μM, phenformin 100 μM, and irinotecan 1 μM are applied in combination; and FIG. 10B illustrates a result obtained by identifying inhibitory effects on proliferation of pancreatic cancer cell lines, caused in a case where gossypol 5 μM, phenformin 100 μM, or irinotecan 1 μM is applied alone, in a case where gossypol 5 μM and phenformin 100 μM are applied in combination, or in a case where gossypol 5 μM, phenformin 100 μM, and irinotecan 1 μM are applied in combination.

FIG. 11 illustrates a result obtained by identifying synergistic inhibitory effects on proliferation of pancreatic cancer cells, caused by combined treatment with gossypol, phenformin, and another anti-cancer agent, in various pancreatic cancer cell lines:

FIG. 11A illustrates a result obtained by identifying inhibitory effects on proliferation of pancreatic cancer cell lines, caused in a case where gossypol 5 μM, phenformin 100 μM, or gemcitabine 1 μM is applied alone, in a case where gossypol 5 μM and phenformin 100 μM are applied in combination, in a case where gossypol 5 μM and gemcitabine 1 μM are applied in combination, or in a case where gossypol 5 μM, phenformin 100 μM, and gemcitabine 1 μM are applied in combination; and FIG. 11B illustrates a result obtained by identifying inhibitory effects on proliferation of pancreatic cancer cell lines, caused in a case where gossypol 5 μM, phenformin 100 μM, or paclitaxel 20 nM is applied alone, in a case where gossypol 5 μM and phenformin 100 μM are applied in combination, in a case where gossypol 5 μM and paclitaxel 20 nM are applied in combination, or in a case where gossypol 5 μM, phenformin 100 μM, and paclitaxel 20 nM are applied in combination.

MODE FOR INVENTION

Hereinafter, the present invention will be described in detail.

As described above, pancreatic cancer is cancer that is difficult to diagnose and treat as compared with cancers of other parts. Thus, an effective therapeutic method is needed therefor, and studies for obtaining a synergistic effect by combined administration of anti-cancer agents at low concentrations are being conducted.

In a case of treating pancreatic cancer using the pharmaceutical composition for preventing and treating pancreatic cancer of the present invention, it is possible to achieve a significant inhibitory effect on proliferation of pancreatic cancer cells and tumor growth with only low concentrations of drugs. Thus, the pharmaceutical composition is effective in that it can specifically kill only pancreatic cancer without affecting survival of normal cells.

Accordingly, the present invention provides a pharmaceutical composition for preventing and treating pancreatic cancer, containing gossypol and phenformin as active ingredients.

"Gossypol" in the composition provided in the present invention has a role as an inhibitor of ALDH expression and activity in cells. Specifically, gossypol acts as an inhibitor of ALDH expression and activity in a cellular mechanism, in which ALDH produces NADH in the intracellular serine-folate mechanism and ATP is generated therefrom, and thus induces intracellular ATP deficiency so that cancer cells can be killed. The gossypol has a structure of the following Formula 1:

[Formula 1]

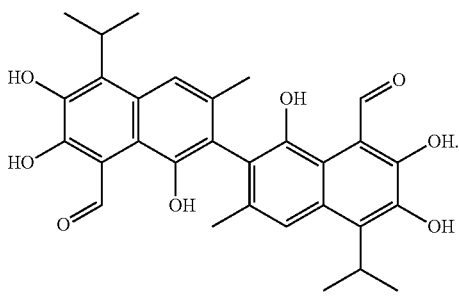

"Phenformin" in the composition provided in the present invention serves as an inhibitor for the mitochondrial complex I in cells. Specifically, phenformin can decrease the mitochondrial membrane potential by inhibiting activity of the mitochondrial complex I, which eventually results in decreased intracellular synthesis of ATP so that cancer cells can be effectively killed. The phenformin has a structure of the following Formula 2:

[Formula 2]

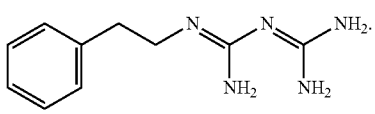

Gossypol and phenformin contained, as active ingredients, in the composition provided in the present invention may encompass all ranges of equivalents thereto which are recognized by those skilled in the art as exhibiting the same or similar level of pharmacological effects. Specifically, for the gossypol and the phenformin, pharmaceutically acceptable salts, hydrates, or solvates thereof may be selected and used.

In the pharmaceutical composition of the present invention, combined administration of the gossypol and the phenformin allows a significant synergistic effect to be obtained in terms of effects of inhibiting proliferation of pancreatic cancer and inducing apoptosis thereof. Here, the gossypol and the phenformin may be mixed in a molar ratio of 1:10 to 1:500. Specifically, it is more preferable that the gossypol and the phenformin be mixed in a molar ratio of 1:10 to 1:200. From the viewpoint of obtaining a significant prophylactic and therapeutic effect on pancreatic cancer by using anti-cancer agents at low concentrations through the pharmaceutical composition of the present invention, it is more preferable that the gossypol and the phenformin be mixed in a molar ratio of 1:10 to 1:100.

More specifically, the pharmaceutical composition of the present invention may contain gossypol at a concentration of 1 to 20 μM, wherein phenformin may be mixed therewith at a concentration that makes the above-mentioned mixing ratio, and thus phenformin can be selectively used by those having ordinary skill in a concentration range of 10 μM to 10 mM, preferably 10 μM to 4 mM, and more preferably 10 μM to 2 mM. In addition, the pharmaceutical composition of the present invention may contain phenformin at a concentration of 50 μM to 1 mM, wherein gossypol may be mixed therewith at a concentration that makes the above-mentioned mixing ratio, and thus gossypol can be selectively used by those having ordinary skill in a concentration range of 2 μM to 100 μM, preferably 5 μM to 100 μM, and more preferably 10 μM to 100 μM.

In a specific example of the present invention, the present inventors have identified that increased levels of ALDH expression and activity are exhibited in pancreatic cancer cells (FIGS. 1 and 2). In this connection, the present inventors have identified that proliferation of pancreatic cancer cells is significantly inhibited in a case where gossypol, an ALDH inhibitor, is applied, and that an inhibitory effect on proliferation of pancreatic cancer cells can be also exhibited by treatment with phenformin (FIG. 3). In this connection, the present inventors have identified that in a case where gossypol and phenformin are mixed and applied in combination to pancreatic cancer cells, a remarkably increased inhibitory effect on proliferation of pancreatic cancer cells is exhibited as compared with an experimental group in which each of these compounds is applied alone (FIG. 4).

Accordingly, the present inventors checked intracellular ATP production levels in order to investigate the cause by which a synergistic effect in terms of inhibitory effects on pancreatic cancer can be exhibited in a case where gossypol and phenformin are applied in combination. As a result, the present inventors have identified that increased intracellular ATP deficiency is exhibited in a case where gossypol and phenformin are applied in combination, as compared with a group in which gossypol or phenformin is applied alone (FIG. 6); and similarly, the present inventors have identified that the mitochondrial membrane potential is also significantly decreased, through which an increased ATP deficiency effect can be exhibited (FIG. 7).

In another specific example of the present invention, in order to identify whether a therapeutic effect on pancreatic cancer can be exhibited at an in vivo level by combined administration of gossypol and phenformin, the present inventors xenotransplanted pancreatic cancer cells into mice and applied thereto gossypol and phenformin via oral administration. As a result, the present inventors have identified that levels of increase in weight and volume of pancreatic cancer are remarkably decreased by combined administration of gossypol and phenformin (FIGS. 8 and 9).

In yet another specific example of the present invention, in order to identify a therapeutic effect on pancreatic cancer by administration of a triple drug in which irinotecan is used in combination with gossypol and phenformin, the present inventors checked a cell proliferation inhibitory effect on pancreatic cancer cells, caused by such a triple drug. As a result, the present inventors have identified that proliferation inhibitory activity against pancreatic cancer cells can be increased to exhibit a synergistic effect in a case where gossypol, phenformin, and irinotecan are combined and the resulting triple combination is applied, as compared with a case where gossypol and/or phenformin is/are applied alone or in combination (FIG. 10). From the viewpoint that a synergistic effect can be further increased in a case where irinotecan is mixed, gemcitabine or paclitaxel was used for combined administration instead of irinotecan. As a result, the present inventors have identified that an inhibitory effect on proliferation of pancreatic cancer cells is increased as compared with a case where only gossypol and phenformin are applied (FIGS. 10 and 11).

Therefore, in the present invention, gossypol is an inhibitor of ALDH expression and activity and serves to induce intracellular ATP deficiency so that cancer cells can be killed; and phenformin is an inhibitor for the mitochondrial complex I and decreases the mitochondrial membrane potential so that a synergistic effect can be exhibited in an ATP deficiency phenomenon. Thus, it is possible to provide a significantly increased inhibitory effect on growth of pancreatic cancer in a case where gossypol and phenformin are applied in combination, as compared with a case where each of these compounds is applied alone.

In addition, in a case where gossypol and phenformin are mixed in a concentration range provided in the present invention and applied to treatment of pancreatic cancer, it is possible to effectively treat pancreatic cancer in that apoptotic effects on pancreatic cancer are remarkably increased by combined administration thereof even at a concentration range in which a significant therapeutic effect on pancreatic cancer cannot be obtained by administration of gossypol or phenformin alone. In particular, in pancreatic cancer, high levels of ALDH expression and activity are exhibited. However, gossypol can inhibit expression and activity of ALDH and thus increase an intracellular ATP deficiency effect, wherein phenformin can cause the ATP deficiency effect to be synergistically exhibited, through which a therapeutic effect on pancreatic cancer can be exhibited. Thus, the pharmaceutical composition of the present invention is effective in that it can specifically kill only pancreatic cancer without affecting survival of normal cells.

In addition, the pharmaceutical composition for preventing and treating pancreatic cancer of the present invention may further contain an anti-cancer agent. Here, the anti-cancer agent that can be used is preferably at least one selected from the group consisting of nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate.chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminoglutethimide, anagrelide, navelbine, fadrozole, tamoxifen, toremifene, testolactone, anastrozole, letrozole, vorozole, bicalutamide, lomustine, and carmustine, but is not limited thereto. The anti-cancer agent may have an ALDH inhibitory activity like gossypol, or may be a biguanide-based drug like phenformin. Specifically, the anti-cancer agent is more preferably at least one selected from the group consisting of irinotecan, gemcitabine, and paclitaxel. More specifically, the anti-cancer agent may encompass all ranges of equivalents thereto which are recognized by those skilled in the art as exhibiting the same or similar level of pharmacological effects. For the anti-cancer agent to be selected, a pharmaceutically acceptable salt, a hydrate, or a solvate thereof may be selected and used.

In the pharmaceutical composition of the present invention, a significant synergistic effect can be obtained in effects of inhibiting proliferation of pancreatic cancer and inducing apoptosis thereof, through combined administration of the gossypol, the phenformin, and the anti-cancer agent. Here, the gossypol, the phenformin, and the anti-cancer agent may be mixed in a molar ratio of 0.1 to 10:10 to 500:1. Specifically, it is more preferable that the gossypol, the phenformin, and the anti-cancer agent be mixed in a molar ratio of 1 to 7:50 to 200:1. From the viewpoint of obtaining significant prophylactic and therapeutic effects on pancreatic cancer by using the anti-cancer agent at a low concentration through the pharmaceutical composition of the present invention, the gossypol and the phenformin are mixed in a molar ratio of 2.5 to 5:100:1.

More specifically, the pharmaceutical composition of the present invention may contain the selected anti-cancer agent at a concentration of 20 nM to 10 µM, wherein the gossypol and the phenformin can be mixed at concentrations that make the above-mentioned mixing ratio. That is, the gossypol can be selectively used by an ordinary skilled person in a concentration range of 0.002 µM to 100 µM, preferably 0.02 µM to 70 µM, and more preferably 0.05 µM to 50 µM. In addition, the phenformin can also be mixed in the above-mentioned mixing ratio, and thus can be selectively used by an ordinary skilled person in a concentration range of 0.2 µM to 5 mM, preferably 1 µM to 2 mM, and more preferably 2 µM to 1 mM.

In a case where the composition of the present invention is used as a medicine, the pharmaceutical composition of the present invention may be made into preparations in the form of the following various oral or parenteral dosage forms and administered at the time of clinical administration, but is not limited thereto.

Examples of the formulations for oral administration include tablets, pills, light/soft capsules, liquids, suspensions, emulsions, syrups, granules, and elixirs. These formulations contain, in addition to active ingredients, a diluent (for example, lactose, dextrose, sucrose, mannitol, sorbitol, cellulose, and/or glycine) and a lubricant (for example, silica, talc, stearic acid and a magnesium or calcium salt thereof, and/or polyethylene glycol). The tablets may contain a binder such as magnesium aluminum silicate, starch paste, gelatin, methyl cellulose, sodium carboxymethyl cellulose and/or polyvinylpyrrolidone, and may optionally contain a disintegrant such as starch, agar, and alginic acid or a sodium salt thereof, or an azeotropic mixture and/or an absorbent, a colorant, a flavor, and a sweetener.

The pharmaceutical composition of the present invention may be administered parenterally, and the parenteral administration is performed by subcutaneous injection, intravenous injection, intramuscular injection, or intrapleural injection. Here, in order to make the composition prepared into a formulation for parenteral administration, gossypol and phenformin are mixed with a stabilizer or a buffer in water to produce a solution or suspension, which may be then prepared into an ampoule or vial unit dosage form. The composition may be sterilized and/or contain an auxiliary agent such as a preservative, a stabilizing agent, a wetting agent or an emulsifying agent, a salt and/or buffer for regulation of osmotic pressure, and other therapeutically useful materials. The composition may be made into a preparation according to mixing, granulation, or coating which is a conventional method.

In addition, a dosage of the pharmaceutical composition of the present invention to the human body may vary depending on the patient's age, body weight, gender, dosage form, health condition, and severity of disease. The dosage is usually 0.001 to 1,000 mg/day, and preferably 0.01 to 500 mg/day, based on an adult patient weighing 60 kg, and may be administered once to several times a day at certain time intervals depending on the judgment of a doctor or a pharmacist.

In addition, the present invention provides a preparation for oral administration, containing, as active ingredients, gossypol and phenformin, or pharmaceutically acceptable salts, hydrates, or solvates thereof.

In addition, the present invention provides a preparation for oral administration, containing gossypol and phenformin, or pharmaceutically acceptable salts, hydrates, or solvates thereof, with an anti-cancer agent further contained.

The preparation for oral administration of the present invention may exhibit a synergistic therapeutic effect for 60 days or longer. Specifically, in a case where gossypol or phenformin is administered alone, it should be expected that an anti-cancer effect is exhibited through repeated administration thereof due to its short duration of pharmacological effect. On the contrary, in a case where gossypol and phenformin are administered in combination, or in a case where gossypol, phenformin, and an additional anti-cancer agent are administered in combination, tumor growth inhibitory and cancer therapeutic effects can be consistently exhibited as compared with the case where gossypol or phenformin is administered alone, and thus such cases can be effective as compared with repeated administration of the drug.

The preparation for oral administration of the present invention may be a sustained-release or controlled-release preparation. In a case of the sustained-release preparation, gossypol and phenformin can be simultaneously released. In a case of the controlled-release preparation, release may be regulated such that gossypol and phenformin, or phenformin and gossypol, can be released in a sequential manner.

In the preparation for oral administration of the present invention, the further contained anti-cancer agent may be at least one selected from the group consisting of irinotecan, gemcitabine, and paclitaxel.

Hereinafter, the present invention will be described in more detail with reference to examples. These examples are merely to illustrate the present invention, and it would be apparent to those skilled in the art that the scope of the present invention is not construed as being limited by these examples.

Example 1

Identification of Aldehyde Dehydrogenase (ALDH) Expression and Activity Levels in Various Pancreatic Cancer Cell Lines In order to identify changes in ALDH expression and activity levels in pancreatic cancer, various pancreatic cancer cell lines were checked.

Specifically, Panel, ASPC-1, Miapaca2, SNU-213, SNU-324, SNU-410, Capan1, Capan2, or Bxpc-3 cells were cultured. Then, the cells were disrupted to obtain a cell extract, and the cell extract was subjected to immunoblot analysis. Expression levels of various ALDH isoforms were respectively identified using respective anti-ALDH antibodies.

As a result, as illustrated in FIG. 1, it was identified that expression levels of ALDH isoform proteins are significantly increased in various pancreatic cancer cell lines. In a case where a comparison is made in various pancreatic cancer cell lines, it was identified that ALDH expression levels of ALDH 1A3, 3A2, and 4A1 are significantly high as compared with the other ALDH isoforms.

In addition, Aldefluor activity analysis was performed to identify ALDH activity in each type of the cells. IMR90 or 293 cell line which represents normal cells; Miapaca2, Panel, SNU-213, SNU-324, or ASPC-1 cell line which is a Kras-mutant pancreatic cancer cell line; or BXPC-3 cell line which is a Kras wild-type pancreatic cancer cell line was cultured, suspended in Aldefluor assay buffer containing ALDH substrate (BODIPY™-aminoacetaldehyde-diethyl acetate, BAAA-DA), and cultured at 37° C. for 45 minutes. Then, fluorescence intensity of the cells was detected through the FL-1 channel of a flow cytometer (BD Biosciences, San Jose, Calif., USA).

As a result, as illustrated in FIG. 2, it was identified that ALDH activity is increased, as a whole, in various pancreatic cancer cell lines as compared with a normal cell control group. This increase was particularly noticeable in pancreatic cancer with KRAS mutation.

Example 2

Identification of Inhibitory Effect of Gossypol or Phenformin on Growth of Pancreatic Cancer Cells It was identified whether gossypol or phenformin can respectively exhibit an inhibitory effect on growth of cancer cells in pancreatic cancer.

Specifically, each type of various pancreatic cancer cell lines, Miapaca-2, Panc-1, Aspc-1, SNU-410, SNU-324, and Bxpc-3 cells, was cultured, during which each type of cells was inoculated into a 96-well plate at a density of 5,000 to 20,000 cells/well depending on an amplification period of culture time. After inoculation, gossypol or phenformin was added to each well and incubated in a $CO_2$ incubator for 24 hours. Then, the cells were fixed by adding 50% (w/v) cooled trichloroacetic acid (TCA) to each well so as to become a final concentration of 10%. The supernatant other than the fixed cells was removed and the plate was washed about five times with tap water and then air dried. After drying, 0.4% (w/v) sulforhodamine B buffer solution containing 1% acetic acid was added to each well, and the plate was left to stand at room temperature for 10 minutes so that the cells were stained. After staining the cells, the plate was washed 5 times with 1% acetic acid to remove unstained dye, and then air dried. The stained dye was immobilized with 10 mM trizma base, and then absorbance was measured at 515 nm using a plate reader.

As a result, as illustrated in FIG. 3, in a case where gossypol or phenformin is added to each type of the pancreatic cancer cells, proliferation of the cancer cells was significantly inhibited and a complete inhibitory effect on cell proliferation was exhibited 48 hours after treatment with the drug. From this, it was identified that each of gossypol and phenformin can exhibit a cell proliferation inhibitory effect on each type of the pancreatic cancer cells.

Example 3

Identification of Inhibitory Effect on Growth of Cancer Cells, Caused by Combined Treatment with Gossypol and Phenformin <3-1> Identification of Inhibitory Effect on Growth of Pancreatic Cancer Cells, Caused by Combined Treatment with Gossypol and Phenformin Each of gossypol and phenformin exhibited a proliferation inhibitory effect on each type of the pancreatic cancer cells. In this connection, it was intended to identify whether an inhibitory effect on proliferation of pancreatic cancer can be increased in a case where gossypol and phenformin are mixed.

Specifically, Miapaca2, Panc-1, or Aspc-1 cells were cultured. Each type of the cultured cells was treated with a mixed drug obtained by mixing gossypol 5 μM and phenformin 100 μM, or gossypol 10 μM and phenformin 500 μM, and cultured in the same manner. Then, it was identified in the same manner as in Example 2, through SRB assay, whether a synergistic effect is exhibited, in terms of inhibition of cell growth in pancreatic cancer cells, by mixed administration of gossypol and phenformin.

As a result, as illustrated in FIG. 4, in a case where gossypol or phenformin was applied alone, significant inhibition of cell growth was not exhibited due to a low drug concentration applied. On the contrary, in a case where gossypol and phenformin are mixed and applied to cells, a cell proliferation inhibitory effect was remarkably increased. Specifically, in a case where gossypol 5 μM and phenformin 100 μM, or gossypol 10 μM and phenformin 500 μM are mixed and the resulting mixed drug is applied to pancreatic cancer cells, a complete inhibitory effect on cell proliferation was exhibited 48 hours after treatment with the drug.

<3-2> Identification of Whether Normal Cells are Killed by Combined Treatment with Gossypol and Phenformin It was identified that a significant cell growth inhibitory effect on pancreatic cancer cells is exhibited in a case where gossypol and phenformin are applied in combination. Thus, it was intended to identify whether gossypol and phenformin also exhibit apoptotic activity against a normal cell line, not pancreatic cancer cells.

First, the normal epithelial cell line IMR90 was cultured. Then, the cultured cells were treated with a single drug of gossypol 10 μM or phenformin 100 μM, or a mixed drug obtained by mixing them, and culture was performed for 24, 48, and 72 hours in total. The medium was removed from the cultured cells, and the cultured cells were washed twice with cold PBS. Centrifugation was performed at 1,400 rpm for 3 minutes, and then a binding buffer solution was added thereto at a concentration of 1×10$^6$ cells/mL. 100 μM of the buffer solution was transferred to a 5-mL culture tube, and 5 μl of each of Annexin V-FITC and propidium iodide (PI) was added thereto. The tube was slowly vortexed to perform mixing, and then incubated for 15 minutes in a dark room at room temperature. After the incubation, a binding buffer solution (400 μl) was added thereto and a level of increase in cell death was checked by flow cytometry.

As a result, as illustrated in FIG. 5, it was identified that a significant increase in cell death is not exhibited over time in IMR90 cells treated with gossypol, phenformin, or a mixture thereof. From this, it was concluded that gossypol and phenformin of the present invention do not exhibit a significant apoptotic effect on normal cells as compared with cancer cells, and thus can be used as cancer cell-targeting drugs.

Example 4

Identification of ATP Production Inhibitory Effect Caused by Combined Administration of Gossypol and Phenformin It was identified that a synergistic effect can be exhibited, in terms of inhibitory effects on growth of pancreatic cancer cells, by combined administration of gossypol and phenformin. Thus, it was intended to identify what causes such a synergistic effect. Since gossypol is known to be an inhibitor for ALDH, an ATP production level in pancreatic cancer cells was checked in a case where gossypol and phenformin are applied.

Specifically, Miapaca2, Panc-1, or Aspc-1 cells were cultured. Each type of the cultured cells was treated with a mixed drug obtained by mixing gossypol 5 μM and phenformin 500 μM, and cultured in the same manner. Then, an intracellular ATP level was checked with the ATP Colorimetric/Fluorometric Analysis Kit (BioVision, Milpitas, Calif., USA) according to the protocol provided by the manufacturer. The cultured cells were divided into 1×10$^6$ cells and 100 μl of ATP assay buffer was added thereto to dissolve the cells. Then, centrifugation was performed at 15,000×g for 2 minutes at 4° C., to separate only the supernatant. 2 to 50 μl of the separated supernatant was transferred to a 96-well plate, and then an ATP assay buffer was added to a final volume of 50 μl per well. Thereafter, an ATP reaction mixture containing 44 μl of ATP assay buffer, 2 μl of ATP probe, 2 μl of ATP converter, and 2 μl of developer mixture was added to the 96-well plate at 50 μl per well and mixing was performed. After the mixing, the plate was left to stand at room temperature for 30 minutes in a dark room, and absorbance was measured at 570 nm using a microplate reader. In order to compare relative ATP levels in the measured values, relative absorbance values obtained in a case where the respective drugs are applied were compared, based on the absorbance values for pancreatic cancer cells to which gossypol and phenformin had not been added, so that intracellular ATP levels were compared.

As a result, as illustrated in FIG. 6, an intracellular ATP level was decreased even in a case where each of gossypol and phenformin is applied alone, as compared with a control group with no drug treatment; however, an ATP level was further significantly decreased in pancreatic cancer cells to which gossypol and phenformin had been mixed and applied in combination. From this, it was identified that a synergistic effect can be exhibited, in terms of intracellular ATP inhibitory effects, by combined treatment with the drugs.

Example 5

Identification of Mitochondrial Membrane Potential-Decreasing Effect Caused by Combined Administration of Gossypol and Phenformin In Example 4, it was identified that a synergistic effect can be exhibited, in terms of ATP production inhibitory effects, by combined administration of gossypol and phenformin. Thus, it was also intended to identify whether there is a change in activity of phenformin. Since phenformin is known to be an inhibitor for the mitochondrial complex I, it was identified whether a change in mitochondrial membrane potential level is caused by combined administration of gossypol and phenformin.

Specifically, Miapaca2, Panc-1, or Aspc-1 cells were cultured. Each type of the cultured cells was treated with a mixed drug obtained by mixing gossypol 5 μM and phenformin 100 μM, or gossypol 5 μM and phenformin 1 mM, and cultured for 24 hours in the same manner. Then, each cell culture was dispensed into a chamber slide (for fluorescence microscopy analysis) or a 6-well plate (for flow cytometry analysis). The dispensed culture was treated with 100 nM tetramethylrhodamine ester (TMRE), which is a fluorescent probe, and reaction was allowed to occur for 20 minutes. After the reaction, the cells were washed with cold PBS and fluorescence development of the cells was measured with a Zeiss LSM510 fluorescence microscope (Carl Zeiss, Oberkochen, Baden-Wurttemberg, Germany). Along with this, fluorescence intensity was analyzed on a flow cytometer using the 585 nm (FL-2) channel.

As a result, as illustrated in FIG. 7, 24 hour-culture of the cells treated with each of the drugs showed that in a case where gossypol 5 μM, phenformin 100 μM, or phenformin 1 mM is applied alone, the mitochondrial membrane potential is exhibited at a similar or increased level as compared with the control group with no drug treatment. On the contrary, it was identified that the mitochondrial membrane potential is remarkably decreased in pancreatic cancer cells to which gossypol and phenformin have been applied in combination.

Example 6

Identification of Anti-Cancer Effect Caused by Combined Administration of Gossypol and Phenformin in Pancreatic Cancer Model It was identified in vitro that combined treatment with gossypol and phenformin can exhibit a synergistic effect, in terms of inhibitory effects on growth of cancer cells, as compared with a case where each of gossypol and phenformin is applied alone. Thus, it was later identified whether an inhibitory effect on pancreatic cancer can be exhibited at an in vivo level.

First, 6- to 8-week-old Balb/c-nu mice (Central Lab. Animal, Highland Heights, Ky., USA) were prepared to make a pancreatic cancer mouse model. In addition, Miapaca2 pancreatic cancer cell line was cultured at $5.0 \times 10^6$ cells, and subcutaneously injected into the prepared mice with a 1-ml syringe. The mice were bred for 2 weeks, and divided into four groups in total, with each group containing 6 mice. The four groups were used as a solvent control group (10% DMSO, 40% PEG, 50% PBS), a group in which 40 mg/kg/100 μl of gossypol is administered alone, a group in which 100 mg/kg/100 μl of phenformin is administered alone, and a group in which gossypol+phenformin are administered in combination, respectively. To each mouse group was orally administered once a day the solvent or the drug, and the mice were bred in the same environment for a total of 61 days.

While breeding the mice, body weights and tumor sizes in each mouse group were checked every 3 days and averaged. A size of the initial tumor after injection of pancreatic cancer cells was determined using a caliper. A tumor volume was calculated using the following Equation 1.

$$\text{volume}(mm^3) = \frac{\text{long diameter} \times \text{short diameter}^2}{2} \qquad [\text{Equation 1}]$$

As a result, as illustrated in FIGS. 8 and 9, it was identified that body weights in a mouse model in which a pancreatic cancer tumor grows are not significantly different among respective experimental groups, whereas a significant difference is exhibited in tumor volume and weight depending on drug treatments. In a mouse model into which a pancreatic cancer tumor had been transplanted through injection of a pancreatic cancer cell line, a solvent control group having not received a drug continuously exhibited an increase in tumor volume. On the contrary, a group to which each of gossypol and phenformin had been applied alone exhibited a tendency that a level of increase in tumor volume is somewhat decreased. However, a further synergistic effect was exhibited, in terms of such inhibitory effects on tumor volume increase, in a case where gossypol and phenformin are administered in combination; and it was identified that there is no significant tumor increase even after a pancreatic cancer mouse model has been bred for 60 days in total. Even in a case where after the breeding ends, tumor size and weight are compared at the sacrifice of the mice, it was identified that a level of increase in tumor weight and size is remarkably decreased in the model group to which gossypol and phenformin have been administered in combination, as compared with the model group to which gossypol or phenformin has been administered alone.

Example 7

Identification of Inhibitory Effect on Growth of Cancer Cells, Caused by Combined Treatment with Gossypol, Phenformin, and Anti-Cancer Agent It was identified that a significant anti-cancer effect on pancreatic cancer can be exhibited in a case where gossypol and phenformin are mixed. Thus, it was intended to identify whether a synergistic effect can be exhibited in terms of anti-cancer activity through an approach (triple combination) in which gossypol and phenformin are mixed with irinotecan and the resulting three drugs are simultaneously applied.

Specifically, Miapaca2, Panc-1, CAPAN1, CAPAN2, ASPC-1, SNU-213, SNU-324, or BXPC-3 cells were cultured. Each type of the cultured cells was treated with gossypol, phenformin, or irinotecan alone, or with a mixed drug thereof. After the drug treatments, the cells were cultured for 48 hours, and then, it was identified in the same manner as in Example 2, through SRB assay, whether a synergistic effect is exhibited, in terms of inhibition of cell growth in pancreatic cancer cells, by mixed administration of gossypol, phenformin, and irinotecan. As a control group, an untreated group with no drug treatment was used, and a relative cell proliferation level in each drug-treated group was expressed and calculated as a percentage as compared with the control group.

As a result, as illustrated in FIG. 10, it was identified that a proliferation level in pancreatic cancer cells is significantly decreased in the experimental group in which irinotecan has been further applied at a concentration of 1 μM, as compared with the group in which gossypol or phenformin has been administered alone (FIGS. 10A and 10B). It was identified that a proliferation level in pancreatic cancer cells is further decreased in the double drug-treated group in which gossypol and phenformin have been applied in combination, as compared with the group in which gossypol or phenformin has been administered alone. In the triple drug-treated group in which gossypol, phenformin, and irinotecan had been applied in combination, it was identified that an inhibitory effect on proliferation of pancreatic cancer cells is remarkably increased so that not only proliferation of pancreatic cancer cells can be inhibited but also an apoptotic effect thereon can be simultaneously exhibited.

In addition, a proliferation level in pancreatic cancer cells was checked by applying, as an anti-cancer agent to be applied in combination with gossypol and phenformin, gemcitabine or paclitaxel instead of irinotecan and then performing SRB assay in the same manner.

As a result, as illustrated in FIG. 11, it was identified that a proliferation level in pancreatic cancer cells is significantly decreased in both of the experimental group in which gossypol, phenformin, and gemcitabine have been applied in combination, and the experimental group in which gossypol, phenformin, and paclitaxel have been applied in combination, as compared with the experimental group in which the double drug of gossypol and phenformin has been applied in combination, so that a synergistic effect is exhibited in terms of anti-cancer activity against pancreatic cancer cells (FIGS. 11A and 11B).

The invention claimed is:
1. A method for treating pancreatic cancer, comprising administering to a patient in need thereof a pharmaceutical composition which comprises gossypol, phenformin, and an anticancer agent, or pharmaceutically acceptable salts thereof, as active ingredients, wherein the anticancer agent is at least one selected from the group consisting of irinotecan, gemcitabine, and paclitaxel, wherein the pharmaceutical composition comprises the gossypol, the phenformin, and the anti-cancer agent in the form of being mixed in a molar ratio of 0.1to 10:10 to 500:1.

2. The method according to claim 1, wherein the gossypol and the phenformin exhibit a synergistic therapeutic effect for 60 days.

3. The method according to claim 1, wherein the pharmaceutical composition is a sustained-release or controlled-release preparation.

4. The method according to claim 1, wherein the pharmaceutical composition is a preparation for oral administration.

* * * * *